(12) United States Patent
Sarstedt

(10) Patent No.: US 6,922,851 B2
(45) Date of Patent: Aug. 2, 2005

(54) LONG-TERM URINE COLLECTION SYSTEM

(75) Inventor: Walter Sarstedt, Nümbrecht (DE)

(73) Assignee: Sarstedt AG & Co., Numbrecht (DE)

( * ) Notice: Subject to any disclaimer, the term of this patent is extended or adjusted under 35 U.S.C. 154(b) by 0 days.

(21) Appl. No.: 10/715,896

(22) Filed: Nov. 14, 2003

(65) Prior Publication Data

US 2004/0148686 A1 Aug. 5, 2004

(30) Foreign Application Priority Data

Nov. 20, 2002 (EP) .............................. 02025930

(51) Int. Cl.$^7$ .............................................. A47K 11/00
(52) U.S. Cl. ........................ 4/144.1; 600/573; 422/102
(58) Field of Search .................... 4/114.1, 144.1–144.3; 600/573–575, 580; 422/102; 73/427

(56) References Cited

U.S. PATENT DOCUMENTS

| | | | | |
|---|---|---|---|---|
| 2,776,691 A | * | 1/1957 | Tupper | .................... 220/256.1 |
| 4,428,384 A | * | 1/1984 | Raitto | ......................... 600/573 |
| 6,126,024 A | * | 10/2000 | Ramirez et al. | ........... 215/12.1 |
| 6,616,893 B1 | * | 9/2003 | Pham | .......................... 422/58 |

* cited by examiner

*Primary Examiner*—Justine R. Yu
*Assistant Examiner*—Huyen Le
(74) *Attorney, Agent, or Firm*—Herbert Dubno; Andrew Wilford

(57) ABSTRACT

A long-term urine-collection kit has a large-capacity can having a wide mouth, a small-capacity cup having a rim dimensioned to sit in the mouth, and a removable cover fittable over the mouth of the can when the cup is sitting in the mouth. The capacity of the can is enough, e.g. 2–3 l, to hold a day's urine, and the capacity of the cup is enough, e.g. 400–500 ml, to hold a single urination.

12 Claims, 3 Drawing Sheets

LONG-TERM URINE COLLECTION SYSTEM

FIELD OF THE INVENTION

The present invention relates to a system for collecting urine over a long term, e.g. 12 or 24 hours. More particularly this invention concerns a urine-collection kit for home use.

BACKGROUND OF THE INVENTION

In order to determine how the kidneys adjust to changing physiologic needs over a long period, it is standard to collect all urine produced for 24 hours. Since substances are excreted by the kidneys at different rates and amounts, in particular the concentration of catecholamine and its derivatives, during the day such a long-term collection of all urine generated over a 24-hour period provides a wealth of usable and normally fairly accurate information.

The catecholamine level in particular is important in detection and treatment of sympatho-adrenal tumors. Catecholamine is however fairly fragile so that it must be protected from excessive temperatures, light, or oxygen or it will break down. Thus when catecholamine levels are being checked, the urine-collection container is made opaque and is provided with a reagent, normally an acid, serving to stabilize the catecholamine. Such a stabilizer is not, however, needed when the urine is being collected to test for a kidney stone as acidification is not needed.

Thus to collect urine over a 24-hour period on an outpatient basis, the patient must be provided with a can of 2 to 3 liter capacity. Once the 24-hour sample has been collected and all of the deposits have been mixed together, the laboratory decants a portion of the contents into a smaller bottle and tests it, normally by centrifuging to start with. The balance in the large can is dumped. This decanting is particularly difficult as the bigger can has a wide mouth to ease urinating into it, so that accurately pouring into a much smaller bottle is virtually impossible to do without making a mess. Furthermore just urinating into the large container can be a problem, especially once it is largely filled and, thus, fairly heavy.

These problems are all compounded by the use of a stabilizing reagent used for acidification of the combined specimens. Typically nitric, sulfuric, or acetic acid at a fairly high concentration is used. Such an acid is normally poured or provided in the large collection can at the start of the collection period, so that the user must be careful not to spill any of this acid and to avoid any splashback. Acid burns are thus a significant risk. When the large can is first used the acid is at maximum concentration so that the acid-burn risk is at its greatest. This risk decreases as the can is filled, but the ever-heavier can becomes increasingly difficult to hold and use, particularly for a female patient.

OBJECTS OF THE INVENTION

It is therefore an object of the present invention to provide an improved long-term urine collection system.

Another object is the provision of such an improved long-term urine collection system which overcomes the above-given disadvantages, that is which is easier to use than the prior-art systems.

SUMMARY OF THE INVENTION

A long-term urine-collection kit has according to the invention a large-capacity can having a wide mouth, a small-capacity cup having a rim dimensioned to sit in the mouth, and a removable cover fittable over the mouth of the can when the cup is sitting in the mouth. The capacity of the can is enough, e.g. 2–3 l, to hold a day's urine, and the capacity of the cup is enough, e.g. 400–500 ml, to hold a single urination.

Thus with this system the patient does not have to manipulate the large and ever-heavier can. Instead he or she simply urinates into the cup and then pours the cup into the can. Then the cup is fitted back to the mouth of the can and its removable cover is replaced to safely and inoffensively contain the collected urine and cup.

The cup according to the invention is elastically deformable. Thus it can easily be deformed to form a sort of pitcher spout, making it easy to pour its contents into the can. Since the cup and can have mouths of substantially the same size, it is relatively easy once the 24-hour collection is done to transfer some of it to the cup from the can, and then from the cup to the specimen container.

The can mouth and cup rim in accordance with the invention are of circular shape and the rim has an outwardly projecting ridge that can sit atop the can mouth. Thus the cup upwardly closes the can when in place, and the can's cover covers and contains them both. This makes it possible for the patient, if necessary, to transport the collection can if, for instance, he or she is not in one place during the entire collection time.

According to another feature of the invention a closable specimen container is provided inside the cup. This specimen container has a threaded cap, and the cup has a removable cover over its rim. The specimen container is inside the cup under the removable cover of the cup. Thus the doctor or laboratory supplies the patient with a simple package that has the dimensions of the large collection can. The patient takes off the can's cover, then pulls out the cup and strips off its cover, which can be a tear-off foil, so as to be able to remove and set aside the specimen cup. After the collection is complete, the urine is mixed and some of it is decanted via the cup to the specimen container for return to the laboratory or doctor.

It is also possible to provide an openable bottle holding reagent inside the cup. This reagent bottle can be inside the specimen container or secured to its cover. Either way, the reagent bottle is neatly held inside the package when it is delivered to the user and is separated from the cup with the specimen container for later use. The reagent is poured into the large can before the first urine deposit is made in it.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
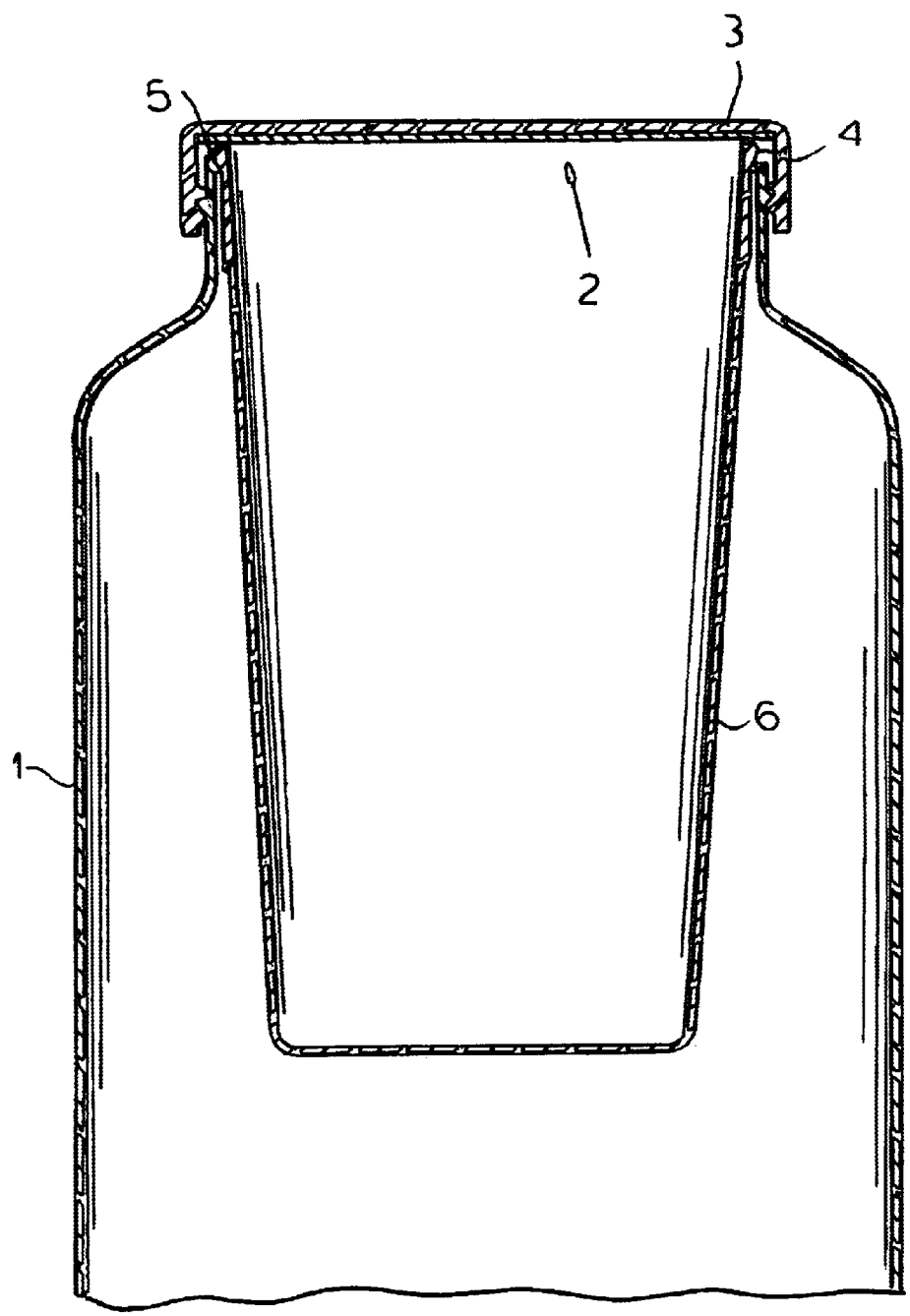
FIG. 1 is a vertical section through a collection kit according to the invention when ready for use.

As seen in FIG. 1, urine is collected over a 24-hour period in a. 2-liter to 3-liter plastic can 1 having a wide mouth 2 fitted with a screw-on cover or cap 3. A smaller cup 6 of 400 ml to 500 ml capacity has an outwardly projecting rim 4 that sits on an outer edge 5 of the mouth 2. The cup 6 therefore fits snugly in the mouth 2 so that, when the cap 3 is in place, the cup 6 and can 1 are both effectively closed.

For use the patient separates the cup 6 from the can 1, urinates into the cup 6, and then pours the specimen from the cup 6 into the can 1. Thus the patient does not have to manipulate the larger can 1, a job that becomes increasingly inconvenient as it fills. The cup 6 is made of relatively light and easily elastically deformed plastic so it can be deformed when pouring its contents into the can 1, thereby making the mouth of the cup 6 something like a pitcher spout and eliminating any possibility of spillage as the cup's contents are poured into the can 1. Even if the can 1 contains acid for stabilizing the urine, pouring the contents of the cup 6 into it is much easier than actually urinating into the acid-filled can, so the possibility of acid burns is greatly reduced.

Figure 2:
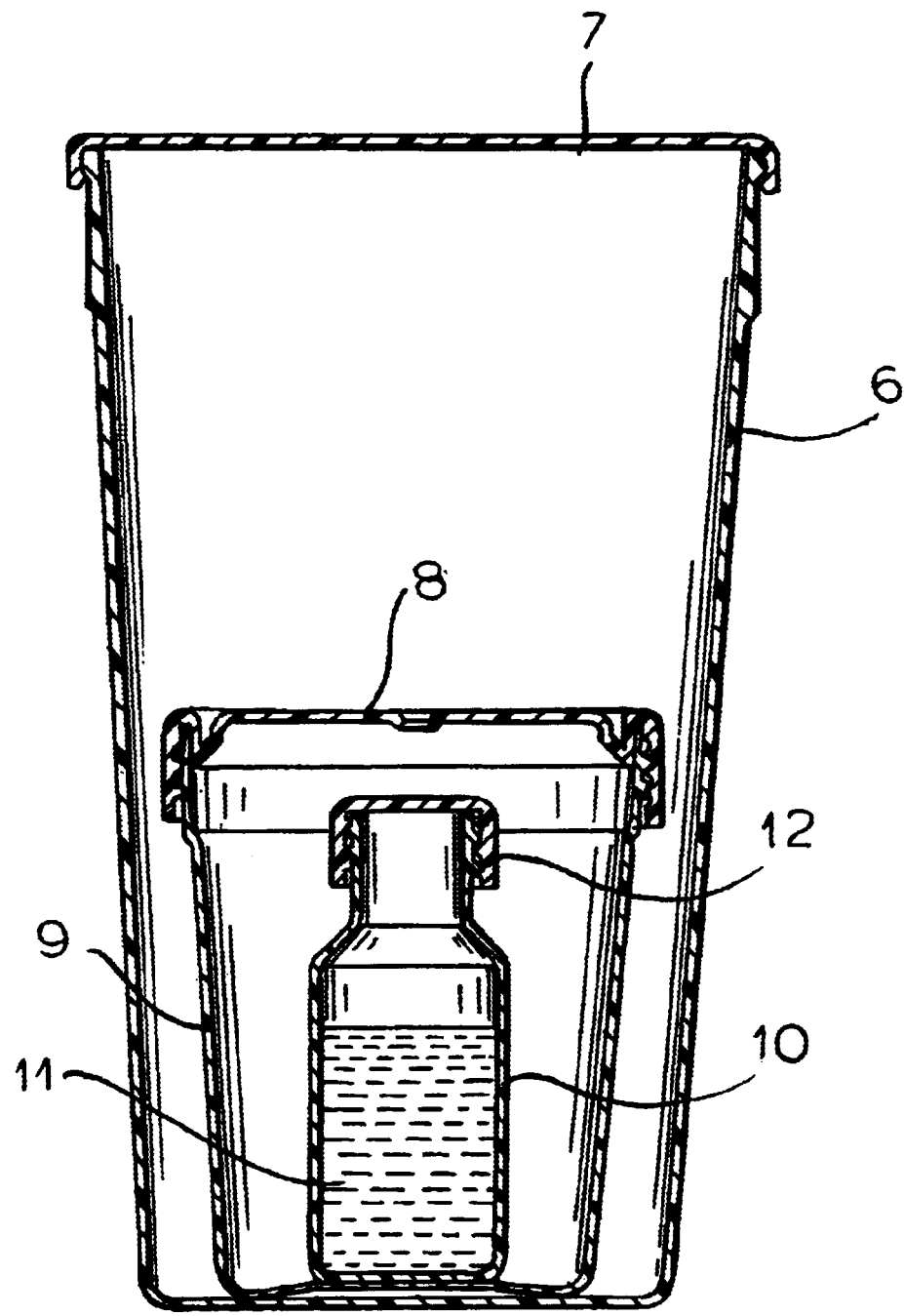
FIGS. 2 and 3 are detail views of a part of the kit as supplied to the user in two separate embodiments.
Figure 3:
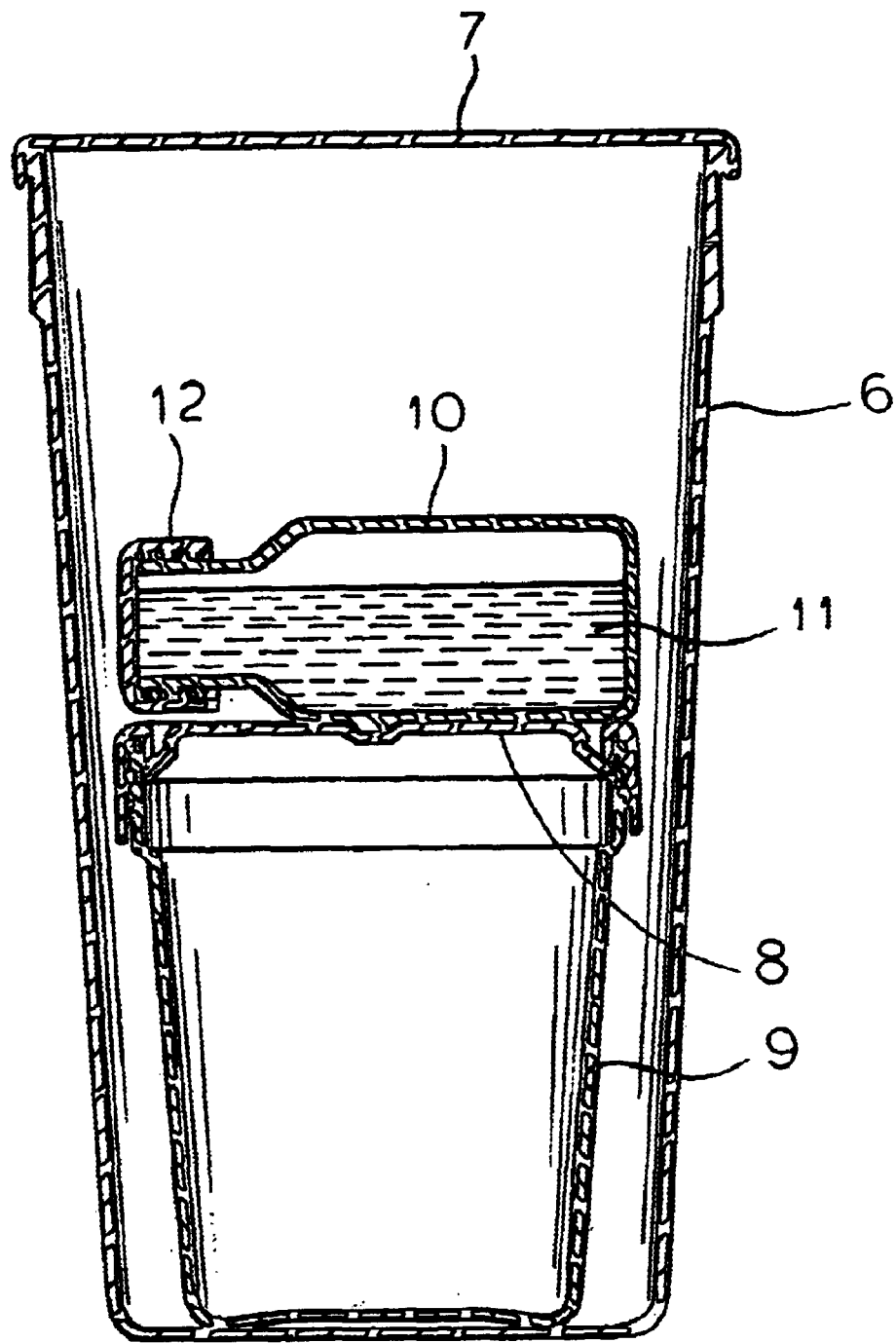

The collection kit is supplied to the patient with the cup 6 equipped as shown in FIG. 2 or 3. Thus the top of the cup 6 is closed by a cover or foil 7 that intended to be removed and discarded. The cup 6 holds a smaller specimen container 9 having a removable screw cap 8. In addition the cup 6 holds a bottle 10 of a reagent 11, here acid, with a screw cap 12. This acid bottle 10 can either be held inside the container 9 as shown in FIG. 2 or secured to its lid 8 as shown in FIG. 3. The cover 7 can carry instructions for the patient about what to do with the acid bottle 10 and specimen container 9. This container 9 can be dimensioned to fit the standard centrifuge used with urine specimens.

Before the first urine deposit is made, the patient removes the cap 3 and lifts out the cup 6 containing the container 9 and bottle 10. The cover 7 is stripped off and discarded and the container 9 and bottle 10 are taken out of the cup 6. The bottle 10 is separated from the container 9 and the container 9 with its lid 8 is set aside. The cap 12 is taken off the bottle 10 and its acid 11 is poured into the can 1.

Then, as mentioned above, the patient urinates into the cup 6 and pours its contents into the can 1 to mix with the acid 11 therein. After each deposit is made, the cup 6 is set back in the mouth 2 of the can 1 and its lid 3 is secured in place.

Once the collection is complete, that is after 24 hours, the capped can 1 is shaken to thoroughly mix its contents, and then a small amount is decanted into the container 9. The can 1, its contents, and the cup 6 are then discarded and the filled and capped container 9 is returned to the doctor or laboratory.

I claim:

1. A long-term urine-collection kit comprising:

a large-capacity can having a wide mouth;

a removable small-capacity cup having a rim dimensioned to sit in the mouth;

a removable closable specimen container inside the cup; and a removable cover fittable over the mouth of the can when the cup is sitting in the mouth.

2. The urine-collection kit defined in claim 1 wherein the cup is elastically deformable.

3. The urine-collection kit defined in claim 1 wherein the can mouth and cup rim are of circular shape and the rim has an outwardly projecting ridge that can sit atop the can mouth.

4. The urine-collection kit defined in claim 1 wherein the specimen container has a threaded cap.

5. The urine-collection kit defined in claim 1 wherein the cup has a removable cover over its rim, the specimen container being inside the cup under the removable cover of the cup.

6. The urine-collection kit defined in claim 5 wherein the removable cover of the cup is a tear-off foil.

7. The urine-collection kit defined in claim 1, further comprising an openable bottle holding reagent inside the cup.

8. The urine-collection kit defined in claim 7 wherein the specimen container has a threaded cap.

9. The urine-collection kit defined in a claim 8 wherein the openable bottle is inside the specimen container.

10. The urine-collection kit defined in claim 8 wherein the openable bottle is secured to the threaded cap of the specimen container.

11. The urine-collection kit defined in claim 1 wherein the can has a capacity of at least about 2 l.

12. The urine-collection kit defined in claim 11 wherein the cup has a capacity of at least about 400 ml.

* * * * *